United States Patent [19]

Burger

[11] Patent Number: 4,680,173

[45] Date of Patent: Jul. 14, 1987

[54] AEROSOL DISPENSING SYSTEM

[75] Inventor: Norman D. Burger, 11621 Segrell Way, Culver City, Calif. 90230

[73] Assignees: Norman D. Burger, Los Angeles; Nicholas A. Mardesich, Palos Verdes Estates, both of Calif. ; a part interest

[21] Appl. No.: 252,306

[22] Filed: Apr. 9, 1981

Related U.S. Application Data

[63] Continuation-in-part of Ser. No. 193,350, Oct. 2, 1980, which is a continuation of Ser. No. 789,639, Apr. 28, 1977, abandoned, which is a continuation-in-part of Ser. No. 727,799, Oct. 1, 1976, abandoned.

[51] Int. Cl.$^4$ .......................... A61K 7/38; A61K 9/12
[52] U.S. Cl. ......................................... 424/47; 424/68; 424/69
[58] Field of Search ....................... 424/68, 47, 46, 66, 424/65

[56] References Cited

U.S. PATENT DOCUMENTS

| | | | |
|---|---|---|---|
| 3,088,874 | 5/1963 | Geary et al. | 424/47 |
| 3,169,095 | 2/1965 | Thiel | 424/46 |
| 4,110,427 | 8/1978 | Kalat | 424/361 |

FOREIGN PATENT DOCUMENTS

| | | | |
|---|---|---|---|
| 6613943 | 4/1968 | Switzerland | 424/47 |
| 987301 | 3/1965 | United Kingdom | 424/46 |

*Primary Examiner*—Dale R. Ore

*Attorney, Agent, or Firm*—Beehler, Pavitt, Siegemund, Jagger, Martella & Dawes

[57] ABSTRACT

An aerosol dispensing system includes a container having a valve-controlled opening for dispensing the container contents, which include hydrocarbon-adsorbent solids such as silica, hydrocarbon propellant adsorbed on such solids, and a weight ratio of hydrocarbon propellant to adsorbent solids ranging up to about 65 parts by weight of the contents, and a liquid composition that may include water, organic oils, alcohols, dispersed and dissolved metals, and metal salts.

Water-encapsulating silica permits use of water in aerosol compositions, but prevents mixing of water with other substances in the composition until the composition is dispensed as an aerosol.

Aerosol systems including containers with a valve-controlled opening and a valve for dispensing the container contents benefit from the addition of a capillary dip tube extending from the valve into the container contents where the contents are highly viscous. The capillary dip tube increases the velocity of the contents, and keeps them cohesive during movement through the tube.

Aerosol system containers having a valve-controlled opening and a vapor tap valve for dispensing the container contents permit the aerosol dispensing of flammable compositions at controlled rates with acceptable flame extensions by dispersing vapor in the product emerging from the valve opening.

14 Claims, No Drawings

AEROSOL DISPENSING SYSTEM

This application is a continuation-in-part of application Ser. No. 193,350 filed Oct.2, 1980, which is a continuation of application Ser. No. 789,639 filed Apr. 28, 1977, now abandoned and which in turn is a continuation-in-part of application Ser. No. 727,799 filed Oct. 1, 1976, now abandoned, by Norman D. Burger.

This invention relates to an aerosol dispensing system that avoids the use of halogenated hydrocarbon propellants, and permits the dispensing of compositions having a wide range of viscosities with inexpensive propellants from conventional containers. The invention also relates to non-corrosive aerosol compositions for use in corrodible aerosol containers. Further, the invention relates to systems for increasing the flow rate of aerosol compositions from conventional aerosol containers by using a capillary dip tube. Still further, the invention relates to systems for dispensing flammable aerosols from conventional containers using valve-controlled openings to disperse vapor into the dispensed product.

Aerosol dispensing systems of many kinds are well known and widely utilized. Most of the known aerosol propellant systems rely upon halogenated hydrocarbons, principally fluorocarbons, as propellants, but these propellants are now known to be degrading the earth's ozone layer. Moreover, these propellants are becoming increasingly expensive, and most aerosol systems that use them require high concentrations of propellant, and low concentrations of other ingredients, including active ingredients, and are therefore quite wasteful.

This invention provides aerosol systems that can propel compositions having a wide range of viscosities with relatively inexpensive propellants, and particularly hydrocarbon propellants, that do not damage the ozone layer of the earth, and that are safe and nonflammable in this system.

More specifically, this invention provides an aerosol system for use with conventional containers having a valve-controlled opening and a conventional valve for dispensing the contents of the container. This system also permits the dispensing of aqueous compositions from containers even when the aqueous system is highly acid. Importantly, the system permits the use of hydrocarbon propellants in relatively large quantities with virtually no flammability, as measured by standard industry tests.

The new system comprises a wet composition that may have a viscosity in the range of about 0.5 centistokes to about 10,000 centistokes, or of 50 seconds or even longer measured with the No. 3 Zahn cup, and may have a pH ranging from highly acid, e.g., 1–2, to highly alkaline, e.g., 14–15. The composition comprises at least three categories of constituents:

(a) Hydrocarbon-adsorbent solids such as high surface area amorphous silicas, in an amount sufficient to adsorb substantially all of the hydrocarbon propellant, optionally including lesser amount of water-encapsulating solids;

(b) At least one hydrocarbon propellant, meaning a propellant that is made of carbon and hydrogen atoms only, substantially all of which is adsorbed by the hydrocarbon-adsorbent solids, and in amount comprising about 6 to about 11 times the weight of the hydrocarbon-adsorbent solids; and (c) A liquid composition that is present in an amount sufficient to make the composition wet, and which may contain water. Where water forms part of the liquid composition, the weight ratio of water to water-encapsulating solids must be in the range of about three to one to about five to one. The balance of the liquid composition may include such substances as organic oils and alcohols, dissolved or suspended metals and metal salts, and chlorinated solvents.

Optionally, the composition may include:

(d) Particulate solids other than hydrocarbon adsorbent solids that have a mesh size in a range that permits them to pass through the openings of valves used in aerosol systems.

The new aerosol system is ideally suited for dispensing deodorants and anti-perspirants of widely varying viscosities and widely varying solids and liquid contents. In this system, these compositions may have viscosities varying from about 0.5 centistokes to about 10,000 centistokes, which means that the compositions may vary from nearly liquid to virtually solid compositions. The new compositions are also adaptable to the dispensing of materials such as insecticides, hairsprays, disinfectants and other space sprays, water- and oil-based paints, and many other food and non-food materials.

The first category of ingredients included in the new composition, the hydrocarbon-adsorbent silicas, may be present in amounts of from 2% by weight to about 8% by weight of the overall composition, preferably about 3.5% to about 4.5% by weight, depending upon the nature and quantity of the hydrocarbon-adsorbent solids, and of the other ingredients, especially the propellant, to be dispensed, the desired dispensing rate, and the presence or absence of water in the composition.

The hydrocarbon-adsorbent solids include, but are not limited to, amorphous silicas and silicates, preferably the amorphous silicas having high surface area, mean ultimate particle size in the order of about 5 to about 20 thousandths of a micron, surface areas greater than about 100 square meters per gram, and densities in the range of at least about 2 pounds per cubic foot. Preferably, such silicas and silicates have a pH that is less than about 7 but pH's above 7 are acceptable. Examples of such hydrocarbon-adsorbent solids are fumed amorphous silicas having a hydrophobic surface such as Tullanox 500 made by Tulco, Inc., of North Billerica, Mass., which has a specific gravity of 2.2, a refractive index of 1.76, a bulk density of 3 pounds per cubic foot, and a surface area of 325 square meters per gram; precipitated amorphous silicas having hydrophobic surfaces such as QUSO ® silicas WR50 and WR82, made by Philadephia Quartz Company, and having surface area of 130 and 120 square meters per gram, respectively, pH of 10.4 and 11.5, respectively, bulk density of 10 pounds per cubic foot and 10 pounds per cubic foot, respectively, and aggregate particle size of 1.8 $\mu$m and 2.3 $\mu$m, respectively; precipitated amorphous silicas having a hydrophilic surface, such as QUSO ® silicas G30 and G32, having ultimate particle size of 14 nm (both), surface area of 300 square meters per gram (both), pH of 8.5 (both), bulk densities of 10 and 4 pounds per cubic foot, respectively, refractive index of 1.45 (both), and specific gravity of 2.1 (both); and silicates such as Philadelphia Quartz Company's magnesium silicate Britesorb ®. The preferred hydrocarbon-adsorbent solids are the high surface area fumed amorphous silicas having hydrophilic surfaces made by Cabot Corporation, and called Cab-O-Sil, especially Cab-O-Sils M-5 and EH-5. These silicas have surface areas of two hundred plus or minus twenty-five square meters per gram and three hundred ninety plus or minus forty square meters per gram, respectively, and densities of about 2.3 pounds per cubic foot. They have a pH, measured as a four percent concentration in water, in the range 3.5 to 4.2. They have a nominal particle size in microns of 0.014 and 0.007, respectively. Both have a bulking value of about 5.5 gallons per hundred pounds, a specific gravity of 2.2, are white in color, and have a silica content greater than 99.8% and a refractive index of about 1.46.

Where the composition nominally contains no water, water-encapsulating solids need not be present, but preferably small amounts such as, for example, up to about 0.2%, will be present to trap moisture in the composition. Where water is present, the water-encapsulating solids must be present in a weight ratio of water to water-encapsulating solids in the range of about 3 to 1, to about 5 to 1, preferably about 4 to 1. The preferred water-encapsulating solids are water-encapsulating silicas. More preferably, the water-encapsulating solids are hydrophobic amorphous silicas such as Tullanox 500, but others such as QUSO ® WR50 and WR82 may also be used.

The new composition permits the use of hydrocarbon propellants without any other kind of propellant besides the hydrocarbon adsorbent solids. Besides the lower cost of these materials than the halogenated hydrocarbons presently used in aerosols, these propellants are nondeleterious to the environment, and are nonflammable in the new system as measured by the CSMA (Chemical Specialties Manufacturers Association) standard flame extension test and open and closed drum tests. These propellants include such hydrocarbons as methane, ethane, propane, n-butane, isobutane, isopentane and pentane. Substantially all of the propellant is adsorbed by the hydrocarbon adsorbent solids of the composition, and the propellant is present in a weight ratio of propellant to hydrocarbon adsorbent solids in the range of about 6 to 1 to about 11 to 1, preferably about 10 to 1. Thus, the amount of propellant may vary from as little as about 10% by weight of the overall composition to as much as about 90% by weight, preferably about 20% to about 50% by weight.

In some cases, the propellant may constitute more than 11 times the weight of the hydrocarbon adsorbent solids, such as where some unadsorbed propellant is desired to insure an adequate supply of propellant to the vapor tap in the vapor tap valve that is used with these compositions. This additional hydrocarbon propellant may raise the ratio of propellant to hydrocarbon adsorbent solids to as high as about 15 to 1.

Although the hydrocarbon propellants may be used alone in the new composition, halegonated hydrocarbons may also be present, if desired. Carbon dioxide, nitrous oxide and other relatively non-liquifiable compressed gases may be present as well, if desired.

Advantageously, this new system permits incorporation of a wide range of percentages by weight of particulate solids, provided the solids have a mesh size that permits their passage through the opening in the stem of valves normally used in aerosol systems. Thus, for example, the mesh size of the solids should not be greater than Number 60 (U.S. Standard Sieve), preferably not greater than 140, and more preferably not greater than about 200. Solids commonly used as fillers and diluents for antiperspirant sprays, particularly those containing aluminum chlorohydrate, include talcs such as Pfizer, Inc.'s Talcron MP50-30 and corn starches such as Vulca-90 and Dri-Flo made by National Starch and Chemical Corporation. Other solids such as sodium carbonate, sodium bicarbonate, and other light metals and light metal salts, e.g., zirconyl hydroxychloride also may be used. One or more of these kinds of particulate solids may be present in the composition, and these solids may constitute up to about 65% by weight of the composition, depending on the maker's desire.

It is essential that the hydrocarbon-adsorbent solids-containing composition used in the aerosol system of this invention be wet, though the viscosity of the composition may vary widely. The composition may include no water at all, but advantageously permits the presence of up to about 25% water on the weight of the composition, preferably not more than about 15% by weight of the composition. Where water is present, water-encapsulating solids must be present in a weight ratio of water to water-encapsulating solids in the range of about 3 to 1 to about 5 to 1, preferably about 4 to 1. The balance of the liquid may be such non-aqueous substances as lower alkyl alcohols, especially ethyl alcohol, organic oils and emollients, such as isopropyl myristate, isopropyl palmitate, and the like. The liquid may also include dissolved solids, suspended solids or both, in amounts ranging from trace quantities up to about 65% by weight of the overall composition. In anti-perspirant compositions that include astringents such as aluminum chloride and aluminum chlorohydrate, the emollient may constitute up to about 50% of the composition.

The compositions of this invention are particularly adapted to the aerosol dispensing of deodorants and anti-perspirants. Modern anti-perspirants commonly include aluminum chlorohydrate and aluminum chloride as active ingredients, and are combined in aerosols with propellants and with inert powders, oily emollients, or some mixture of the two. Consumer preferences dictate a wide range of viscosities and textures in anti-perspirant sprays, ranging from oily to dry and powdery. The system of this invention may be adapted to any anti-perspirant in this range of textures. Thus, for example, where a dry powdery spray is desired, the particulate solids, silica and propellant will constitute a larger percentage of the composition than does the liquid composition.

The use of water-encapsulating solids in this system permits the presence of water in amounts ranging up to about 25%, but preferably ranging up to not higher than about 15%, by weight of the container composition. Aluminum chlorohydrate (ACH) and aluminum chloride (AC) are much more effective anti-perspirants where combined with water than where no water is present in the anti-perspirant composition. The water-encapsulating solids encapsulate water droplets in the container and insulate the water from other materials in the container, and from the inner surfaces of the container. This encapsulation permits the use of materials in the system which would be chemically active if they combined with water. Insulated from water, such materials are, and remain, relatively inert in the container. Upon dispensing through the container valve, however, the shearing action of the spray valve breaks the encapsulation, and frees the water to mix with other constituents dispensed from the container.

Water-encapsulating solids may be used in a wide variety of aerosol compositions besides the solid state aerosols of this invention. Water-encapsulating solids isolate water or water-active substances blended with water from other substances in such compositions. This isolation prevents reaction of water with other substances that would otherwise occur in containers for such compositions. Thus, if the aerosol container includes water-active substances that become corrosive when mixed with water and attack the surfaces of such containers, adding water-encapsulating solids will prevent this. Water-encapsulating solids include, but are not limited to, those amorphous silicas having hydrophobic surfaces, including Tullanox 500 and QUSO ® silicas WR50 and WR82. Where Tullanox 500 is the water-encapsulating solid, the ratio of water or of water plus dissolved water-active solids to the water-encapsulating silicas may be in the range of about 8 to 1 to about 3 to 1.

The water-encapsulating solids are best dispersed with the water, avoiding shearing forces which interfere with the encapsulating mechanism. In aerosol antiperspirant compositions, water-encapsulating solids may be used to isolate water from metal salts such as ACH and AC, or to isolate the mixture of water and such solids from the rest of the composition. As a result, the water/metal salt blend is prevented from attacking the container for the composition, yet the encapsulation is readily broken by the shearing forces exerted on the composition when dispensed from the valve controlling outlet from the container.

The new compositions may be formulated by blending the hydrocarbon adsorbent silicas with the other particulate solids in proportions appropriate for making the desired container composition. The liquid composition is formulated separately, then blended with the solids blend. The combined liquids/solids blend is placed into containers, which are pressurized with the desired quantity of hydrocarbon propellant. Alternatively, the hydrocarbon adsorbent solids may be blended directly with propellant before filling the container with the blend.

Where water is to be part of the composition, the water is preferably added alone to the blend of solids before any other liquid such as an oil is added. The water should be dispersed in the solids at low shear until the water-encapsulating solids have encapsulated the water. Surfactants, if any, should be added to the oil phase, and should constitute not more than about 0.9% of the container composition.

Overall, the new compositions may include about 2% to about 70–75% solids, about 12% to about 55% hydrocarbon propellant, and 0% to about 45% liquids, all based on the weight of the container composition. The viscosity of the compositions may range from about 0.5 centistokes to about 10,000 centistokes, more commonly up to about 5,000–6,000 centistokes, and may therefore accommodate the dispensing of many different kinds of products at many different rates of dispensing, and all of these compositions may be dispensed with conventionally made pressure-tight containers, valves and dip tubes.

It should be apparent that the aerosol system of this invention is radically different from known aerosol formulations, which generally require a low viscosity liquid concentrate, typically slurried or thinned with liquid propellant. Such prior art systems have viscosities anywhere from 0.5 to 250 centistokes. At these viscosities, hydrocarbons such as butane and propane cannot be the propellant in previously disclosed aerosol systems because flammability would be extremely high and hazardous, unless flame retardants such as water are present in substantial quantities.

Accordingly, conventional aerosol formulations cannot tolerate more than about 15% by weight of a hydrocarbon propellant without producing excessive flammability. Flammability has been previously reduced in such formulations by adding harsh solvents such as methylene chloride. Unfortunately, these solvents are undesirable in many formulations, particularly anti-perspirant formulations, because they cause skin irritation and some inhalation toxicity.

The invention, by contrast, provides a solid state propellant system which not only permits, but takes advantage of, higher viscosity formulations to reduce the flammability of hydrocarbon propellants to a safe level. No solvents or thinning agents or flame retardants need be utilized in this system, yet the system produces desirable delivery rates of dispensed product with virtually no flammability.

This new system achieves these highly desirable results by combining appropriate size capillary dip tubes, valve stems, and vapor taps with a unique propellant system that may be substantially all hydrocarbons adsorbed by certain hydrocarbon adsorbent solids to achieve a system that can deliver as little product as 50 to 750 milligrams per second from an aerosol dispenser, and as much as 1.5 to 2 or even more grams per second from the same equipment.

In particular, the vapor tap valve permits the codispensing at a controlled rate of product and propellant together with a considerable quantity of vaporized hydrocarbon propellant to produce a spray that is nonflammable when measured by standard industry tests. The vapor phase of such propellants is considerably less flammable than the liquid phase of the same propellants. Thus, for example, 200 mg/second of vapor phase hydrocarbon propellant dispensed as an aerosol is virtually non-flammable; whereas, 200 mg/sec of the liquid phase of the same dispensed propellant is highly flammable. Preferably, the vapor tap orifice diameter is in the range of about 0.010 to about 0.025 inches, and will ordinarily be no larger in diameter than the diameter of the stem orifice. In these valves, the stem orifice preferably will be in the range of about 0.010 to about 0.030 inches.

The capillary dip tubes used in this system permit control of the rate of product and propellant dispensing. To that end, the inside diameter of the dip tube becomes smaller as the viscosity of the aerosol system's contents increases to produce a sufficient velocity of the contents of the dip tube to the valve, and to produce an acceptable spray from the valve. As the viscosity decreases, the inside diameter of the capillary dip tube increases to reduce the velocity of the contents of the dip tube to the valve, and to produce an acceptable spray from the valve. The preferred vapor tap valve will be joined to a capillary dip tube having an inner diameter in the range of about 0.030 to about 0.040 inches.

Capillary dip tubes and vapor tap valves may be advantageously used to dispense aerosol compositions other than the solid state compositions of this invention from conventional aerosol containers. Thus, if the compositions include at least one flammable constituent that would ordinarily produce an unacceptable flame extension when dispensed, a conventional aerosol container may be fitted with a vapor tap valve to disperse larger quantities of relatively non-flammable vapor into the aerosol spray. This vapor tends to reduce the flammability of the spray, and to shorten the flame extension of the dispensed product. Optionally, such a container may also be fitted with a capillary dip tube which tends to accelerate the container contents toward the valve opening, keeps the container composition cohesive as it moves through the capillary dip tube, and thus minimizes fluttering and sputtering of the aerosol spray as dispensed. Moreover, the capillary dip tube also tends to reduce the quantity of products delivered per unit of time, thus helping to control further the flame extension of the dispensed aerosol composition.

Even where the aerosol composition does not contain a flammable constituent, the capillary dip tube may be used to increase the velocity of product delivered to the valve opening, particularly where the aerosol composition has a high viscosity, such as 5000 centistokes or more.

The flammable constituent in the composition may be the propellant, such as a hydrocarbon propellant, another constituent, such as alcohol or silicone, or both. The capillary dip tube, if any, should have an internal diameter in the range of about 0.020 to about 0.050 inches. Larger diameter dip tubes preclude accelerating highly viscous aerosol compositions therethrough because cavitation occurs in the dip tube. The vapor tap valve should have a vapor tap diameter in the range of about 0.010 to about 0.030 inches, and a stem orifice diameter in the range of about 0.010 to about 0.040 inches. The valve may have one or more than one stem orifice opening, but each of these openings will commonly have a diameter in this range.

The relationship of vapor tap diameter to stem orifice diameter and to capillary dip tube internal diameter may vary depending on the degree of flammability of the aerosol composition. Thus, the vapor tap diameter may be substantially larger than the stem orifice diameter where the aerosol composition is very highly flammable. For example, with aerosol hair spray compositions containing large proportions of such highly flammable constituents as alcohols, the capillary dip tube internal diameter may be 0.030 inches, the vapor tap diameter in the range of 0.015 to 0.025 inches, and the stem orifice diameter in the range 0.010 to 0.016 inches. With the stem orifice diameter substantially smaller than the vapor tap diameter, the aerosol composition as dispensed will contain a large quantity of dispersed vapor, which tends to reduce the flammability and flame extension of the dispensed composition.

The new propellant system of this invention is not limited to use in aerosol spray systems. The propellant system of the invention may also be adapted for use in dispensing such high viscosity products as creams, lotion and gels without foaming or otherwise disturbing the physical state of such products. Because such products are dispensed as relatively viscous liquids, smaller quantities of hydrocarbon propellant, preferably in the range of about 1 or 2% to about 4 or 5%, more preferably about 3%, by weight of the composition, will be sufficient to dispense such high viscosity products with little or no foaming in the dispensed product.

As with the use of the new propellant system in aerosol sprays, the propellant principally comprises at least one hydrocarbon propellant, meaning a propellant that is made of carbon and hydrogen atoms only, substantially all of which is adsorbed by the hydrocarbon-adsorbent solids, in amounts comprising about 6 to about 11 times the weight of the hydrocarbon-adsorbent solids. Unlike the application of this propellant system to aerosol sprays, however, water-encapsulating solds may, but need not, be used. The kinds of hydrocarbon-adsorbent solids and hydrocarbon propellants may be the same as those used in the aerosol spray systems of this invention, and are described in detail above. Further, the weight ratio of hydrocarbon propellant to hydrocarbon-adsorbent solid must be in the range of about 6 to 1 to about 11 to 1, preferably about 10 to 1.

High viscosity products such as creams, lotions and gels may be dispensed from conventional aerosol propellant containers equipped with capillary dip tubes having an internal diameter in the range of about 0.030 to about 0.040 inches, and from standard dispensing valves that may have a stem orifice diameter in the range of about 0.010 to about 0.030 inches. Such valves have no vapor tap.

In summary, then, where the propellant system of this invention is adapted for use in dispensing such high viscosity products as creams, lotions and gels, the dispensing system will be made up of a container equipped with a conventional valve and having a capillary dip tube extending from the valve into the container contents. The contents will comprise from about 1 to about 5% hydrocarbon propellant, and from 1/6th to about 1/11th, more preferably about 1/10th, of the hydrocarbon propellant by weight of hydrocarbon adsorbent solids, based on the weight of the overall composition. The balance of the container contents will be made up of one or more high viscosity products which may or may not contain some particulate solids, some dissolved solids, or both. The viscosity of these composition contents may be up to about 8,000 centistokes.

The following examples illustrate the application of the new aerosol system to the formulation of anti-perspirant aerosol compositions. Unless otherwise indicated, all percentages are by weight based on the weight of the overall composition inside the container, and therefore exclusive of the weight of the container, valve and dip tubes.

EXAMPLE I

Following the method prescribed above, the following composition was formulated:

| Ingredient | Percentage by Weight |
|---|---|
| Cab-O-Sil EH-5 | 4 |
| Cornstarch (Vulca 90) | 15 |
| Aluminum Chlorohydrate | 17 |
| Isopropyl myristate | 31.5 |
| Propellant A46* | 32.5 |
| | 100.0 |

*Blend of propane, isobutane and n-butane, having a vapor pressure of about 46 pounds per square inch gauge.

This composition has a viscosity of about 2,000 centistokes, and dispenses 350 milligrams per second of ingredients from a metal container fitted with a vapor tap valve that has a stem orifice diameter of 0.014 inches, a vapor tap diameter of 0.013 inches, and having a capillary dip tube with an inner diameter of 0.030 inches.

This aerosol composition proved substantially non-flammable in the CSMA test, producing a 0- to 2-inch flame extension measured at six inches from the terminal orifice of the actuator. The composition also passed successfully the open and closed drum tests.

This aerosol composition dispensed more readily from a similar container fitted with a valve having a stem orifice diameter in the range 0.016 to 0.020 inches and a vapor tap diameter of about 0.014 inches.

EXAMPLE II

Following the method prescribed above, the following composition was formulated:

| Ingredient | Percentage by Weight |
|---|---|
| Cab-O-Sil EH-5 | 2.3 |
| Tullanox T500 | 1.3 |
| Cornstarch (Vulca 90) | 30.8 |
| Aluminum Chlorohydrate | 10.0 |
| Isopropyl myristate | 20.0 |
| Propellant A46* | 35.6 |
| | 100.0 |

*Blend of propane, isobutane and n-butane, having a vapor pressure of about 46 pounds per square inch gauge.

This anti-perspirant composition dispenses approximately 350 milligrams per second of ingredients from a metal container fitted with a vapor tap valve with a stem valve diameter of 0.014 inches, and a vapor tap diameter of 0.013 inches, and with a capillary dip tube with an inner diameter of 0.030 inches.

This aerosol composition proved substantially non-flammable in the CSMA test, producing a 0- to 2-inch flame extension measured six inches from the terminal orifice of the actuator. The composition also passed successfully the open and closed drum tests.

This aerosol composition dispensed more readily from a similar container fitted with a valve having a stem orifice diameter in the range 0.016 to 0.020 inches, and a vapor tap diameter of about 0.014 inches.

EXAMPLE III

| Ingredient | Percentage by Weight |
|---|---|
| Cab-O-Sil EH-5 | 3.6 |
| Tullanox T500 | 1.3 |
| Cornstarch (Dri-flo) | 29.5 |
| Aluminum Chlorohydrate | 10.0 |
| Isopropyl Myristate | 14.8 |
| Propellant A46* | 35.6 |
| Water | 5.2 |
| | 100.0 |

*Blend of propane, isobutane and n-butane, having a vapor pressure of about 46 pounds per square inch gauge.

This anti-perspirant composition dispenses approximately 350 milligrams per second of ingredients from a pressure-tight metallic container fitted with a vapor tap valve with a stem valve diameter of 0.014 inches, and a vapor tap diameter of 0.013 inches, and with a capillary dip tube with an inner diameter of 0.030 inches.

This aerosol composition proved substantially non-flammable in the CSMA test, producing 0- to 2-inch flame extension measured six inches from the terminal orifice of the actuator. The composition also passed successfully the open and closed drum tests.

This aerosol composition dispenses more readily from a similar container fitted with a valve having a stem orifice diameter in the range 0.016 to 0.020 inches and a vapor tap diameter of about 0.014 inches.

One of the important features of this invention is the use of a particular form of inorganic powdered silica in such a form as to protect metal containers from corrosion where the metal containers are packed with materials which, in the presence of water tend to cause rust and corrosion within the container. Typical corrosion producing materials are acids and salt compounds, for example, aluminum chlorohydrate, used in astringent antiperspirant formulations.

It is known, for example, from U.S. Pat. No. 3,968,203 issued July 6, 1976 to Spitzer et al, that water soluble aluminum salts, typically aluminum chlorohydrate, cause corrosion when present with water in an aerosol packaging system. Other astringent materials which tend to cause the same problems in the presence of water include the astringent salts of multi-valent cations such as tetravelent salts such as zirconium tetrachloride, zirconium sulfate; trivalent salts such as aluminum sulfate, aluminum chloride, aluminum sulfocarbolate, aluminum chlorohydrate, ferric chloride; and divalent salts such as zinc chloride, zinc sulfate, zinc sulfocarbolate, and mixtures of all of the above salts.

Another problem noted in the above-identified Spitzer et al. patent is that the use of such astringent salts with water, even in small amounts, in an aerosol bomb tends to cause clogging of the aerosol actuator assembly.

Thus, the inorganic silica used in accordance with the present invention, and which is different in chemical, physical and functional properties from conventional colloidal silica, e.c., Cab-O-Sil and the various grades thereof, provides a mechanism by which water may be used in various formulations while eliminating rust and corrosion of the container for the shelf life of the product. In fact, the stability of the packed containers is significant and for an extended period of time.

Typically, the inorganic powdered silica of the present invention is referred to as having the property of "super-hydrophobicity". This property is achived by reacting a low bulk density inorganic powdered silica of high surface area such that the surface is modified by structural groups such as trimethylsiloxyl, siloxane, and hydroxyl, the latter being sterically hindered such that they do not exhibit hydrophobic qualities. Since the siloxane groups are hydrophobic, the result is an extremely hydrophobic surface.

The particle size of the material may vary from 0.007 microns to 15 nm with mean aggregate particles of about 1.5 to 2.5 micrometers. The surface area (by $N_2$ adsorption, B.E.F.) may vary from 120 $m^2/g$ to 225 $m^2/g$. The bulk density may vary from 3.0 to 10 lbs./$ft^3$. The pH (as measured in a water/isopropyl alcohol mixture) may be between 8 and 11.5. Typical materials which are available commonly are Tullanox 500 made by Tulco, Inc. or from Philadelphia Quartz Company under the designation Hydrophobic QUSO® WR Micro Fine Silica, Grade QUSO® WR50 and WR82, for example.

The super-hydrophobic fumed silica materials retain their water repellant properties at temperatures up to 350° C. Some grades of the silica include a surface ammonia of about 0.2% which can be removed by heating at about 400° F. for 10–15 minutes or until the pH drops to about 5.5. Alternatively, about 65% of the ammonia may be removed by exposing the silica to ambient air at room temperature for about 7 days.

Other materials which may be used include a product from Cabot Corporation, Cab-O-Sil M-70TS. This product has a surface area of 200 $m^2$/gram and is rendered hydrophobic by treatment with a silicone oil. Another material is that available from Degussa called Aerosil R-972 which is believed to be a fumed silica treated with a silane to render the surface super-hydrophobic. This material has a pH between 3 and 4.

Two methods may be used in the protection of containers from corrosion. In one, the super hydrophobic fumed silica can be mixed with the can lining material and applied to the inside of the container during manufacture. Presently used vinyl and epoxy can lining materials may be used with about 0.25% by weight of the fumed silica. The anti-corrosive can lining material may be applied to the entire interior of the container or to portions thereof, such as the side seam areas. While this method may be satisfactory for conventional cans and containers, it is not entirely satisfactory for aerosol containers because of the metal components of the aerosol valves. While coating the can body may protect the container metal, the problem of clogging the activator valve cannot be solved solely by coating the container wall.

Thus, it is preferred in the present invention that the super-hydrophobic fumed silica be used as a component of the container contents. Typically, the superhydrophobic fumed silica is present in an amount up to about 5.5% by weight of the total contents of the container, and preferably between 3% to 5% by weight of the container contents.

In the case of aqueous anti-perspirant sprays, the formulation includes an astringent such as aluminum chlorohydrate (ACH), water, talc and emollients such as isopropyl myristate or isopropyl palmitate or mixtures thereof. The ACH, water, talc and emollients are normally not miscible and tend to form an emulsion. The use of the fumed silica of this invention permits the blending of these materials without forming an emulsion. When the above materials are used in accordance with this invention, a stable homogeneous mixture results. Normally, the fumed silica of this invention is used at a ratio of from 10 parts water to one part fumed silica up to 4 parts water to one part silica.

In compounding the material the solids are first dry blended so that the hydrophobic silica is evenly distributed through the mixture. Usually, the solids and other powders including the astringent, e.g., ACH, are dry blended using conventional dry blending equipment such as a high speed blender. After thorough and complete mixing has been accomplished, the proper amount of the hydrophobic silica is added and thoroughly blended and mixed with the other materials.

The second operation includes the gradual addition of water or other aqueous solutions while the material is blended and mixed until all of the liquid phase has been added and thoroughly mixed. In the mixing operation it is preferred to use a shear type of mixer or blender. The resulting mixture is then filtered to aerosol consistency using a filter screen which will keep the particle sizes below 0.004 inches. Typically, a 200 U.S. Standard Filter Screen (0.0029 mil) may be used. The filtering procedure assures that there will be no solid particles of a size big enough to clog or plug the internal metering orifices of the aerosol valve because of the comparatively large size of the particles of the contents.

As a result of preparation of the material as above described, the hydrophobic silica surrounds the small droplets of water or aqueous phase formed as a result of shear mixing. In effect, the water is encapsulated and cannot contact the astringent, i.e., the acid or salt compound which causes corrosion.

Since water increases the effectiveness of the astringent or anti-perspirant material, it is necessary for water to contact that material. If contact takes place within the metal container, there is rust and corrosion of exposed metal. By the present invention, the water is encapsulated and separated from the astringent and the anti-perspirant.

One of the surprising features of this invention is that the flow of the container contents through the aerosol valve operates to break up the encapsulated droplets to release the water for contact with the astringent or antiperspirant. What is surprising is that shaking of a packed container will not release water, but flow through the aerosol valve will release water and in effect activate the astringent before the spray reaches its intended surface.

It is also possible in accordance with the present invention to use the hydrophobic silica to encapsulate dissolved astringents or anti-perspirants which are in aqueous solutions, e.g. ACH solutions. In such an instance, corrosion is prevented because the ACH solution is prevented from contacting any exposed metal in the container. When dispensed, the freed ACH solution is effective for its intended function.

Typical formulae, in addition to that already given are as follows:

| | | |
|---|---|---|
| (a) | ACH | 20 grams |
| | Water | 10 grams (including 2.5 grams of T-500 as described) |
| | Talc | 45 grams |
| | Isopropyl Myristate | 55 grams |
| | A-46 | 72 grams |
| (b) | Isopropyl Myristate | 30 grams |
| | ACH | 20 grams |
| | Talc | 60 grams |
| | EH-5 | 5 grams |
| | T-500 | 3 grams |
| | Water | 12 grams |
| | A-46 | 70 grams |

While the above prior discussion of the use of water-encapsulating solids has centered upon aerosol systems, it is to be understood that any type of aerosol system may be used and the practice of the invention is not limited to the particular aerosol systems discussed, i.e., valve mechanism and valve and dip tube dimensions. Where reduced flame extension is desired, one may use the valve mechanism disclosed, even with hydrocarbon propellants.

Another advantage of the present invention is that the anti-perspirant may be dry blended and mixed as described in one location and transported to another location for aerosol packaging. Since there is no problem with corrosion, the handling equipment need not be constructed of corrosion resistant equipment.

It is understood that the precise formulation of the anti-perspirant aerosol material may vary widely. The advantage of the present invention is that the water-encapsulating technique may be used wherever it is desired to prevent corrosion of exposed metal in the container. The relatively small particles of the super-hydrophobic fumed silica function as an outer phase of a droplet whose inner phase may be water or an aqueous solution including the salts and acids described. The dry blending assures that when the liquid material is added and the shear mixing is used, the water or aqueous solution is broken up into small droplets which are encapsulated due to the hydrophobic nature of the fumed silica.

While the above disclosure sets forth various formulations and procedures, it is understood that modification thereof may be made without departing from the scope of the appended claims.

I claim:

1. In an aerosol system for dispensing an antiperspirant where the system includes a metal container having a valve-controlled spray, a valve for dispensing the contents thereof, and a dip tube extending from said valve to said container contents, a propellant for said system, and wherein said contents includes an anti-perspirant material such as the astringent salts of multivalent cations, divalent astringent salts, trivalent astringent salts, tetravalent astringent salts and aluminum astringent salts, wherein said anti-perspirant material if dissolved in water forms a material corrosive with respect to the exposed metal of said container, the improvement comprising:

a super-hydrophobic powdered fumed silica having a particle size of between 0.007 microns and 15 nm, a surface area of from 120 $m^2/g$ to 225 $m^2/g$ as measured by the nitrogen adsorption, B.E.T., a bulk density of from 3 to 10 lbs./$ft^3$, said super-hydrophobic silica being present in an amount of up to about 5.5% by weight of the container contents, water in an amount sufficient to increase the effectiveness of said anti-perspirant material, and said super-hydrophobic fumed silica encapsulating at least said water to form a multiplicity of encapsulated drops whose outer surface is the fumed silica and whose contents include at least said water, thereby to prevent contact between said water and any exposed metal of said metal container.

2. In an aerosol system of claim 1 wherein said anti-perspirant is in solution with water and wherein said super-hydrophobic fumed silica encapsulates said solution to form a multiplicity of encapsulated drops whose outer surface is said fumed silica and whose contents include said solution.

3. In an aerosol system as set forth in claim 1 wherein said anti-perspirant material is aluminum chlorohydrate.

4. In an aerosol system for dispensing an antiperspirant where the system includes a metal container having a valve-controlled spray, a valve for dispensing the contents thereof, and a dip tube extending from said valve to said container contents, a propellant for said system, and wherein said contents includes an anti-perspirant material such as the astringent salts of multivalent cations, divalent astringent salts, tetravalent astringent salts, trivalent astringent salts and aluminum astringent salts, wherein said anti-perspirant material if dissolved in water forms a material corrosive with respect to the exposed metal of said container, the improvement comprising:

a multiplicity of encapsulated droplets having a particle size of not greater than about 0.004 inches, said droplets including an aqueous inner phase which if it contacts said anti-perspirant material will corrode any exposed metal of said container, said droplets including an outer phase of particles of a super-hydrophobic fumed silica, said outer phase operating to encapsulate said aqueous inner phase while said droplets are within said container and to rupture when said container contents are dispersed, and said water being present in an amount sufficient to activate said anti-perspirant material.

5. In an aerosol system of claim 4 wherein said aqueous phase is water.

6. In an aerosol system of claim 4 wherein said aqueous phase is a solution of water and said anti-perspirant material.

7. In an aerosol system of claim 4 wherein said fumed silica has a particle size of between 0.007 microns and 15 nm.

8. In an aerosol system of claim 4 wherein water is present in an amount of 5.5% or less by weight of said contents.

9. In an aerosol system of claim 4 wherein the ratio of water to said fumed silica is between 10:1 to 4:1.

10. In an aerosol system of claim 4 wherein said fused silica has a bulk density of between 3 and 10 lbs./$ft^3$.

11. A composition for use as an anti-perspirant and to be packaged in a container including exposed metal surfaces, said composition including as the essential ingredients:

a multiplicity of encapsulated droplets having a particle size of not greater than about 0.004 inches, an anti-perspirant material which if contacted by water will corrode any exposed metal surfaces of said container, said encapsulated droplets including an outer phase of a particulate super-hydrophobic fumed silica, said fumed silica having a particle size of less than 0.007 microns, and said encapsulated droplets including an inner phase of aqueous solution.

12. A composition as set forth in claim 11 wherein said inner phase is water and said outer phase prevents contact between said water and said anti-perspirant material.

13. A composition as set forth in claim 11 wherein said inner phase includes dissolved anti-perspirant material and said outer phase prevents said inner phase from contacting exposed metal.

14. A composition as set forth in claim 11 wherein said composition is in the form of a free-flowing dry powder.

* * * * *